Nov. 28, 1967 W. ZOMBORY ETAL Plant Pat. 2,780
DIANTHUS PLANT
Filed Sept. 15, 1966
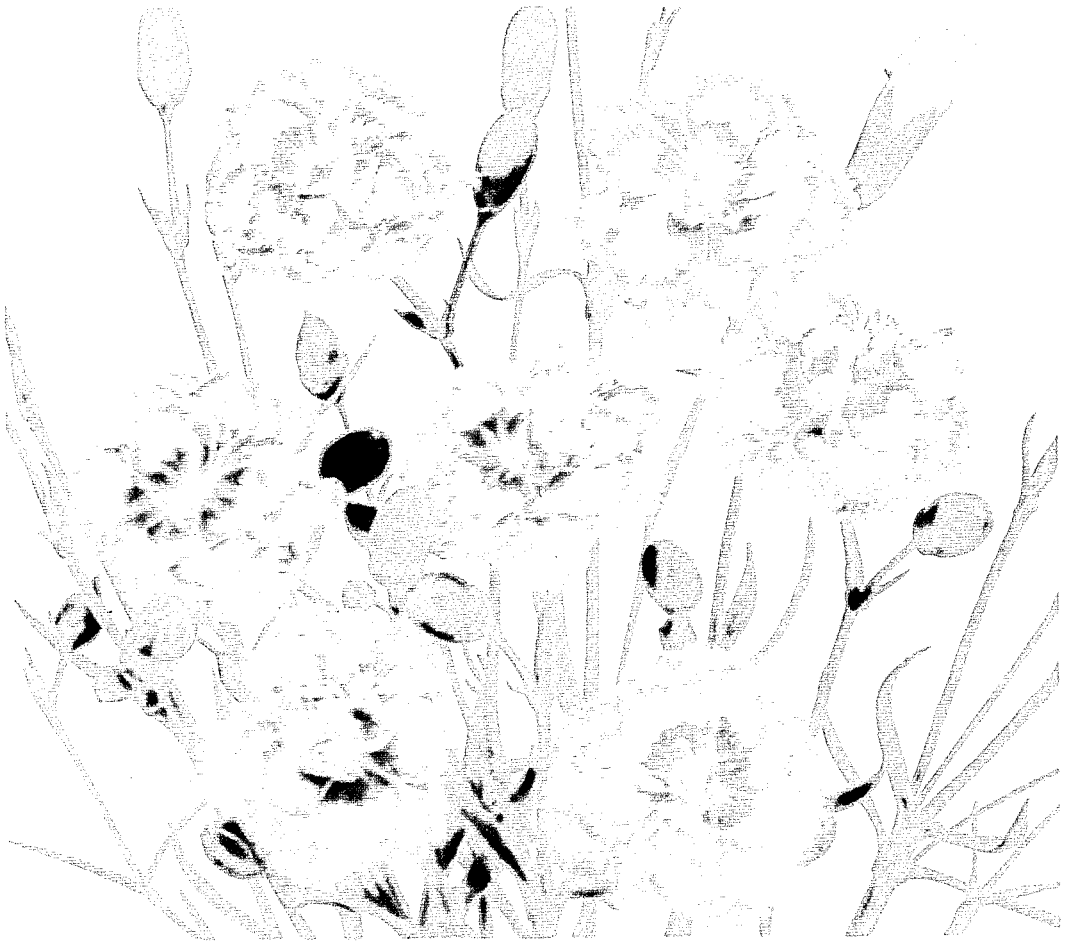
Inventors.
William Zombory
Sophia B. Zombory
By: Robb & Robb
Attorneys.

United States Patent Office

Plant Pat. 2,780
Patented Nov. 28, 1967

2,780
DIANTHUS PLANT

William Zombory and Sophia B. Zombory, Detroit, Mich., assignors to Jackson & Perkins Company, Newark, N.Y., a corporation of New York Filed Sept. 15, 1966, Ser. No. 579,793
1 Claim. (Cl. Plt.—70)

The present invention relates to a new and distinct variety of Dianthus plant, which was originated by us by crossing an unnamed and unpatented Dianthus seedling of unknown parentage with an unnamed and unpatented double laced pink flowered variety of the species botanically known as *"Dianthus allwoodi."*

The primary objective of this breeding was to produce a new and improved dianthus variety having the everblooming habit and compact form of *"Dianthus allwoodi,"* but which bears flowers of a different color than those of this species. This objective was fully achieved, along with other desirable improvements, as evidenced by the following unique combination of characteristics which are outstanding in the new variety and which distinguish it from its parents, as well as from all other varieties of which we are aware:

(1) A compact habit of growth;
(2) Attractive Dark Green foliage;
(3) An everblooming habit;
(4) Frilled and lacy flower petals;
(5) A distinctive and attractive flower color corresponding to La France Pink, with the petals edged with Rose Red, and with a blotch of Carmine in the lower half of the petals; and
(6) A spicy sweet flower fragrance.

Asexual reproduction of our new variety by cuttings, as performed at Detroit, Mich., and also at Newark, N.Y., shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with Ridgway's Color Standards and Nomenclature.

Parentage: Seedling.
*Seed parent.*—An unnamed Dianthus seedling of unknown parentage.

*Pollen parent.*—An unnamed double laced pink flowered variety of the species botanically known as *"Dianthus allwoodi."*

Blooming season: Starts blooming the first year when grown from cuttings, with blooms produced during June and July, and again during September.

*Plant*

Growth: Tall (about 12 to 14 inches); compact.
Leaves: Many bottom leaves in tufts; about 3 inches to 3½ inches long; narrow; thick.
*Color.*—Elm Green, Plate 17, with silvery sheen of Mytho Green, Plate 41.
Flower stem: About 11 to 12 inches long; strong; stiff.
*Color.*—Light Elm Green, Plate 17.

*Flower*

Borne: Mostly on own-branched stalks; bears from 3 to 5 flowers per stem; some of the laterals nearly sessile.
Size: From 2 inches to 2½ inches in diameter.
Petals: From 20 to 25 petals; frilled and lacy.
*Color.*—Upper side—La France Pink, Plate 1, with petals edged with Rose Red, Plate 12, and with a blotch of Carmine, Plate 1 in the lower half of the petals. Reverse side—Hermosa Pink, Plate 1. Claw—White, Plate 53, blended in with Light Turtle Green, Plate 32.
Calyx: Cylindrical; teeth about ½ inch long; erect; splits on wide open flowers.
*Color.*—Courge Green, Plate 17, with teeth Biscay Green, Plate 17.
Bracts: 4 in number; medium size.
*Color.*—Light Cress Green, Plate 31.
Stamens: About 10 in number.
*Color.*—White, Plate 53.
Anthers: Color—Pale Mauve, Plate 25.
Ovary: Small; oval.
Fragrance: Spicy sweet.

We claim:

A new and distinct variety of Dianthus plant, substantially as herein shown and described, characterized particularly as to novelty by the unique combination of a compact habit of growth, attractive Dark Green foliage, an everblooming habit, frilled and lacy flower petals, a distinctive and attractive flower color corresponding to La France Pink, with the petals edged with Rose Red, and with a blotch of Carmine in the lower half of the petals, and a spicy sweet flower fragrance.

No references cited.

ROBERT E. BAGWILL, *Primary Examiner.*